United States Patent
Tyagi et al.

(10) Patent No.: US 8,258,312 B2
(45) Date of Patent: Sep. 4, 2012

(54) PROCESS FOR PREPARING PURE VALSARTAN

(75) Inventors: Om Dutt Tyagi, Hyderabad (IN); Jakka Devendra Rao, Hyderabad (IN); Katukuri Aravind Kumar, Hyderabad (IN); Dammalapati Ventaka Lakshmi Narasimha Rao, Hyderabad (IN)

(73) Assignee: Mylan Laboratories Ltd (IN)

( * ) Notice: Subject to any disclaimer, the term of this patent is extended or adjusted under 35 U.S.C. 154(b) by 132 days.

(21) Appl. No.: 12/666,476

(22) PCT Filed: Jun. 26, 2008

(86) PCT No.: PCT/IN2008/000411
§ 371 (c)(1),
(2), (4) Date: Dec. 23, 2009

(87) PCT Pub. No.: WO2009/001375
PCT Pub. Date: Dec. 31, 2008

(65) Prior Publication Data
US 2010/0197932 A1    Aug. 5, 2010

(30) Foreign Application Priority Data
Jun. 27, 2007 (IN) .......................... 1383/CHE/2007

(51) Int. Cl.
*C07D 249/00* (2006.01)
(52) U.S. Cl. ...................................................... 548/253
(58) Field of Classification Search ................... 548/253
See application file for complete search history.

(56) References Cited

U.S. PATENT DOCUMENTS

| 5,399,578 A | 3/1995 | Buhlmayer et al. |
| 2005/0059827 A1* | 3/2005 | Rukhman et al. ............. 548/254 |
| 2006/0149079 A1 | 7/2006 | Padi et al. |

FOREIGN PATENT DOCUMENTS

| EP | 443983 A1 | 8/1991 |
| EP | 1714963 A1 | 10/2006 |
| WO | 2005/051929 A1 | 6/2005 |
| WO | 2007/054965 A2 | 5/2007 |
| WO | 2007/057919 A2 | 5/2007 |

OTHER PUBLICATIONS

International Search Report, PCT/IN2008/000411, dated Nov. 29, 2010.
Supplementary European Search Report and Opinion for European Application No. 08789911.8 issued Dec. 21, 2011.
Schmidt B et al: "Safe and fast tetrazole formation in ionic liquids", Tetrahedron, Elsevier Science Publishers, Amsterdam, NL, vol. 63, No. 2, Dec. 5, 2006, pp. 492-496, XP005802275.

* cited by examiner

*Primary Examiner* — Susannah Chung
(74) *Attorney, Agent, or Firm* — Lerner, David, Littenberg, Krumholz & Mentlik, LLP

(57) ABSTRACT

An improved process for the preparation of substantially pure valsartan employing suitable reagents such as chelating agent and reaction conditions.

8 Claims, No Drawings

PROCESS FOR PREPARING PURE VALSARTAN

CROSS REFERENCE TO RELATED APPLICATIONS

The present application is a national phase entry under 35 U.S.C. §371 of International Application No. PCT/IN2008/000411, filed Jun. 26, 2008, published in English, which claims the benefit of Indian Patent Application No. 1383/CHE/2007, filed Jun. 27, 2007. The disclosures of said applications are incorporated by reference herein.

FIELD OF THE INVENTION

The invention in general relates to process for preparing substantially pure valsartan. More particularly, but without restriction to the particular embodiments herein after described in accordance with the best mode of practice, this invention relates to an improved process for the preparation of substantially pure valsartan employing suitable reagents and reaction conditions.

BACKGROUND OF THE INVENTION

Valsartan, N-(1-oxopentyl)-N-[[2'-(1H-tetrazol-5-yl)[1,1'-biphenyl]-4yl]methyl]-L-valine, is a known anti-hypertensive agent having the following formula (I):

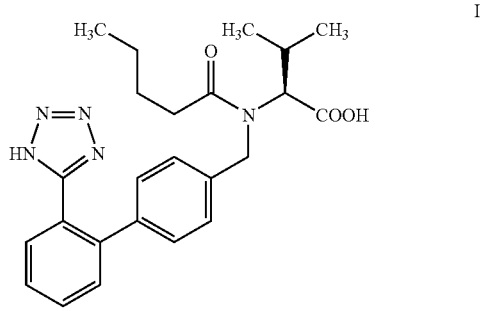

Valsartan is a non-peptide, orally active, specific angiotensin II antagonist, useful in the treatment of hypertension and is commercially available in the market under the brand name DIOVAN™ as 40, 80, 160 and 320 mg tablets.

Valsartan, its pharmaceutically acceptable salts, pharmaceutical compositions comprising valsartan and their use in treating high blood pressure and cardiac insufficiency are disclosed in U.S. Pat. No. 5,399,578 along with its preparation as depicted in scheme 1.

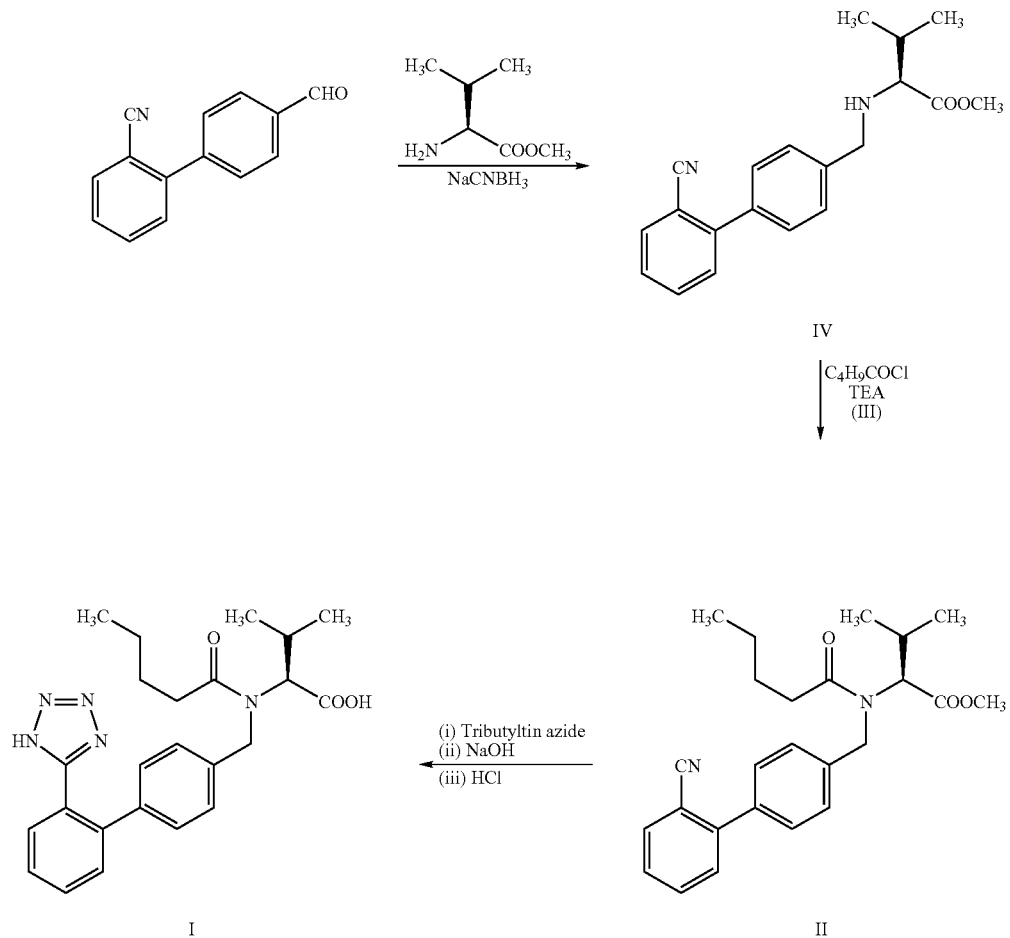

Briefly, the process for the preparation of Valsartan comprises the condensation of compound of formula IV with Valeryl chloride of formula III in the presence of triethylamine and dichloromethane followed by flash chromatography, to give the compound of formula II. The compound of formula II during tetrazole formation is undergo reaction with tributyltin azide and then subsequently hydrolysis using base like sodium hydroxide followed by flash chromatography gives Valsartan of formula I.

The preparation of Valsartan according to the scheme reported above is very complicated and not commercially viable. The synthetic process which involves, inter-alia the use of tributyltin azide leads to increase the tin content in final product as an impurity approx. 20 ppm. It would therefore be highly desirable to provide a process the preparation of substantially pure valsartan, which is commercially viable as well as reduces/removes the contamination of tin content in the final product i.e., Valsartan.

It has now been found an alternative process for the preparation of substantially pure Valsartan which fulfills the above mentioned requirements.

SUMMARY OF THE INVENTION

It is, therefore, an object of the present invention to improve upon limitations in the prior art. These and other object are attained in accordance with the present invention provide wherein there is provided embodiment of an improved process for the preparation of substantially pure Valsartan.

In accordance with one preferred embodiment of the present invention, there is provided a process for the preparation of valsartan free from tin content.

In accordance with another preferred embodiment of the present invention, there is provided a process for the preparation of valsartan using the chelating agent.

DETAILED DESCRIPTION OF THE INVENTION

The disclosed embodiment of the present invention deals with a process for producing substantially pure Valsartan by using chelating agent (scheme 2).

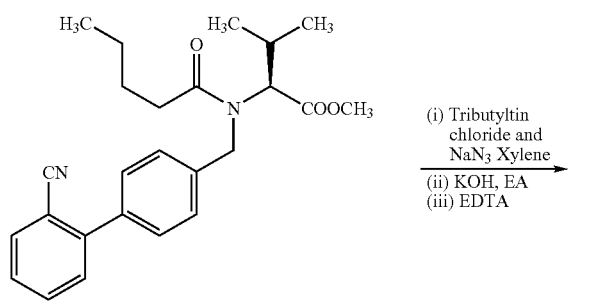

II (i) Tributyltin chloride and NaN₃ Xylene
(ii) KOH, EA
(iii) EDTA

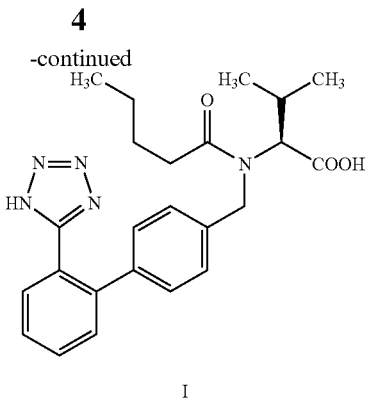

I

The present invention in its aspect is a new, improved, economically and industrially feasible method for preparing substantially pure Valsartan. Valsartan obtained by the process of the invention is in fact substantially pure, and in particular free from tin content. The expression "substantially pure" means a purity degree equal to or higher than 99% and having a tin content in said contaminants equal to or lower than 5 ppm.

The compound of formula II is treated with tributyltin azide in a solvent such as xylene, toluene or mixture thereof at refluxing temperature for a period of 18-36 hrs preferably 24 hrs. The reaction mixture is then cooled to 0-40° C., preferably 25-35° C. followed by quenching with an aqueous base. The base is selected from the group consisting of alkali metal hydroxide or alkaline earth metal hydroxide, preferably sodium hydroxide and potassium hydroxide. The isopropyl ether is added to the reaction mixture under stirring for a period of 6-12 hrs, preferably 8-10 hrs. The organic layer is separated and then pH of the aqueous layer is adjusted with hydrochloric acid to 6.0-8.0 followed by treatment with charcoal. The reaction mixture is filtered followed by washing with an organic solvent. The organic solvent used herein is selected from the group consisting of halogenated hydrocarbons such as dichloromethane, chloroform and carbon tetrachloride. Chelating agent is added to the aqueous layer and stirred for period of 15-45 min, preferably 30 min. The chelating agent used herein is selected from the group consisting of but not limited to ethylenediamine tetraacetic acid (EDTA), diethylenetriaminepentaacetic acid; diethylenetriamine-N,N,N',N',N''-pentaacetic acid (DTPA) and N,N-bis(carboxymethyl)glycine (NTA). The halogenated hydrocarbon is added to the reaction mixture followed by maintaining the pH to 3.0-5.0, preferably 4.0-4.5 with 10% hydrochloric acid and stirred. The halogenated hydrocarbon used herein is dichloromethane, chloroform and carbon tetrachloride, preferably dichloromethane. Layers are separated and organic layer is dried followed by evaporation to dryness to get residue. The obtained residue is then taken in ethyl acetate and optionally treated with charcoal and followed by cooling to get substantially pure valsartan.

The compound of formula II can be prepared from any of the prior art process for the preparation of valsartan.

While the present invention has been described in terms of its specific embodiments, certain modifications and equivalents will be apparent to those skilled in the art and are intended to be included within the scope of the present invention.

The present invention can be illustrated in one of its embodiment by the following non-limiting examples.

Example 1

Compound of formula II (50 gm) was treated with tributyltin azide prepared from reaction of tributyltin chloride (81 gm) and sodium azide (25 gm) in water (62 ml) and extracted in dichloromethane] in xylene at 25-30° C. under N₂ atmosphere under refluxed for 24 hrs. After completion of the reaction, mixture was cooled to room temperature and quenched with aqueous potassium hydroxide (53.8 gm in 800 ml water) with stirring. The isopropyl ether (65 ml) was added to the reaction mixture and stirred followed by the layer separation. Aqueous layer was then treated with charcoal (7 gm) and filtered and washed with dichloromethane (3×50 ml). The pH of the aqueous layer was adjusted to 6.8-7.2 using hydrochloric acid and then treated with charcoal (7 gm) and filtered. EDTA (5 gm) was added to the aqueous solution and pH was adjusted again to 4.0-4.5 using hydrochloric acid and stirred. The aqueous layer was extracted with dichloromethane (3×66.5 ml) and then organic layer was washed with 10% sodium chloride solution. The organic layer was evaporated to dryness to get residue and then residue was taken in ethyl acetate (25 ml) and raised the temperature to 40-45° C. followed by treatment with charcoal (5 gm) and filtered. The reaction mixture was cooled to 18-22° C. and filtered the residue under nitrogen atmosphere. The residue was washed with ethyl acetate and dried.

Certain modifications and improvements of the disclosed invention will occur to those skilled in the art without departing from the scope of invention, which is limited only by the appended claims.

We claim:

1. A process for the preparation of Valsartan, comprising
a) reacting a compound of formula II:

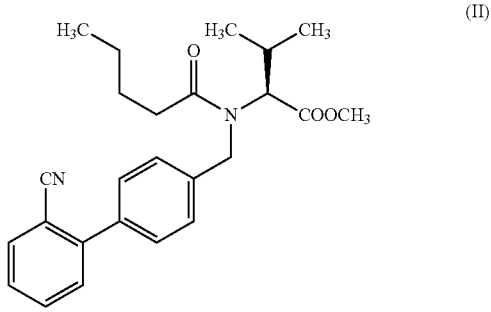

with tributyltin azide in a solvent;

b) quenching the reaction with a base;
c) treating the reaction mixture with charcoal and washing with organic solvent;
d) adjusting the pH of the reaction mixture to 6.0-8.0 using an acid and treating with charcoal and filtering;
e) adding a chelating agent to the reaction mixture;
f) adjusting the pH to 3.0-5.0 using an acid;
g) extracting the aqueous layer with an organic solvent;
h) evaporating the solvent to obtain a residue;
i) taking the residue in ethyl acetate and cooling;
j) filtering and drying the precipitates.

2. The process according to claim 1, wherein the solvent used is xylene, toluene or a mixture thereof.

3. The process according to claim 1, wherein the base is an alkali metal hydroxide or an alkaline earth metal hydroxide.

4. The process according to claim 3 wherein the base is sodium hydroxide or potassium hydroxide.

5. The process according to claim 1, wherein the organic solvent is dichloromethane, chloroform or tetrachloromethane.

6. The process according to claim 1, wherein the acid used is hydrochloric acid.

7. The process according to claim 1, wherein the chelating agent used is ethylene diamine tetraacetic acid.

8. The process of claim 1, wherein the Valsartan obtained comprises no more than 5 ppm of a tin-containing compound.

* * * * *